United States Patent [19]

Fawkes

[11] Patent Number: 4,655,756

[45] Date of Patent: Apr. 7, 1987

[54] TREATED NON-WOVEN MATERIAL

[75] Inventor: David M. Fawkes, Marple, England

[73] Assignee: Imperial Chemical Industries PLC, London, England

[21] Appl. No.: 771,881

[22] Filed: Sep. 3, 1985

[30] Foreign Application Priority Data

Aug. 31, 1984 [GB] United Kingdom ............... 8422070

[51] Int. Cl.$^4$ .............................................. A61F 13/16
[52] U.S. Cl. ................ 604/360; 128/132 D;
424/402; 428/290; 428/913
[58] Field of Search ............... 428/290, 913; 424/27,
424/28, 32; 604/360; 128/132 D

[56] References Cited

U.S. PATENT DOCUMENTS 4,401,712 8/1983 Morrison .............................. 424/27

Primary Examiner—James J. Bell
Attorney, Agent, or Firm—Cushman, Darby & Cushman

[57] ABSTRACT

There is disclosed a non-woven material having a superficial coating of a linear polymeric biguanide in which the recurring unit is of the formula

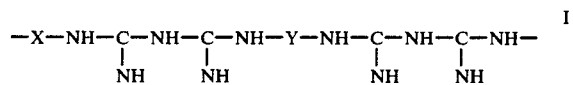

wherein X and Y, which may be the same or different, represent bridging groups in which the total number of carbon atoms in X and Y taken together, directly interposed between the pairs of nitrogen atoms linked thereby, is from 10 to 16, or the salt thereof with an acid. Preferably the polymeric biguanide is polyhexamethylene biguanide dihydrochloride. The material is useful in the form of an article designed for the collection of human body emissions, more particularly disposable nappies to avoid bacterial activity.

9 Claims, No Drawings

TREATED NON-WOVEN MATERIAL

This specification describes a treated non-woven material which is resistant to the activity of microbial species, especially bacteria, and a process for the preparation of such material.

According to the present invention there is provided a non-woven material having a superficial coating of a linear polymeric biguanide in which the recurring unit is of the formula:

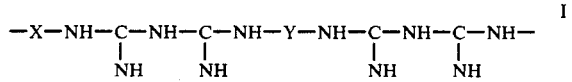

wherein X and Y, which may be the same or different, represent bridging groups in which the total number of carbon atoms in X and Y taken together, directly interposed between the pairs of nitrogen atoms linked thereby, is from 10 to 16, or the salt thereof with an acid.

The bridging groups X and Y, which may be the same or different, preferably comprise polymethylene chains, optionally interrupted by oxygen, nitrogen or sulphur atoms and may incorporate saturated or unsaturated cyclic groups. When the groups X and Y incorporate cyclic groups, the number of carbon atoms directly interposed between pairs of nitrogen atoms include the carbon atoms in the shortest segment of the cyclic group.

In a preferred polymeric biguanide, X and Y are both polymethylene groups containing from 3 to 12 carbon atoms and more preferably X and Y are both hexamethylene. The polymeric biguanide preferably has a molecular weight in the range 500 to 20,000 and contains from 5 to 12 biguanide units.

Especially preferred is a mixture of polymeric biguanides of the formula:

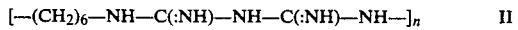

wherein n varies from about 6 to 10, having a number average molecular weight from about 1300 to 2200, preferably in the form of salts with hydrochloric acid.

The polymeric biguanide has broad spectrum of activity, at very low levels, against bacteria, fungi and yeasts, particularly those associated with the human body. Furthermore, it harmless to macrobiotic systems and, in particular, is not a skin sensitiser. It will, therefore, not give rise to problems when applied to articles which will be in direct contact with the skin for extended periods.

The non-woven material is preferably in the form of an article designed for the collection of human body emissions, generally fluid emissions, such as urine, catarrh, excreta and phlegm, which are susceptible to bacterial degradation. Examples of such articles are disposable nappies and incontinence pads, paper handkerchiefs and disposable feminine hygiene pads. When such emissions are in contact with bacteria for an extended period, the bacteria can cause changes in the emissions, and chemical substances therein, which can have deleterious effects on the environment, i.e. the body with which the non-woven material is in contact or the surrounding atmosphere. Thus, when disposable nappies become contaminated with urine bacteria present in the anal region effect chemical reactions in the urine which raise the pH and lead to the formation of malodorous chemicals; one product of bacterial activity in urine is the formation of ammonia. Extended contact of the degradation products with the skin can lead to "nappy rash" and general discomfort to the wearer.

Various attempts have been made to control odours and 'nappy rashes' by incorporating a biocide into disposable nappies (e.g. DC 5700, American Dyestuff Reporter, June 1984, p. 35–45, and chlorhexidine as described in UK No. 1443086, 23.2.73. assigned to Proctor & Gamble) but none have found commercial acceptance.

It has now been found that non-woven materials treated with the polymeric biguanide are particularly suitable for use in the preparation of such articles because of the significant inhibition of bacterial activity when the article becomes contaminated with body emissions.

In addition to protection against bacterial activity in the body emissions absorbed on the material, the polymeric biguanide will also provide protection of the non-woven material itself against bacterial action during storage prior to use.

The non-woven material preferably contains from 100 ppm up to 100,000 ppm, and more preferably from 500 ppm up to 5000 ppm, of the polymeric biguanide.

The non-woven material may be treated with the polymeric biguanide during the preparation of the material by, for example, soaking the constituent fibres in a solution of the polymeric biguanide or spraying the material after formation with a solution thereof. As the polymeric biguanide is readily soluble in water an aqueous solution may be used.

The polymeric biguanide has a strong affinity for cellulosic, and related synthetic, materials which are conventionally used for the preparation of non-woven articles, and it is very efficiently taken up by such materials from an aqueous solution. The polymeric biguanide, in the form of its hydrochloride salt, is extremely soluble in water and aqueous solutions thereof are substantially non-foaming.

Since, the absorbent wadding or cellulosic material of the aforesaid disposable items is the major structural component responsible for absorbing body fluids such as urine, this is the most logical place to locate the bioactive compound. In order that additional drying costs are avoided, such application should preferably take place from aqueous media during pre-existing wet processing stages during manufacture to preclude additional drying costs. In order to ensure uniform uptake of the biocide, such processes involve high speed agitation of the cellulose fibres in aqueous dispersion. In such a process, the water soluble polymeric biguanide is particularly well suited since it is substantially non-foaming. In this respect it is superior to the chlorhexidine cited in UK No. 1443086 which foams to a greater extent and also produces a more stable foam. Furthermore, the use of ethanolic solutions of chlorhexidine disclosed and exemplified in UK No. 1443086 constitute an unacceptable industrial hazard compared with the use of aqueous solutions of the polymeric biguanide. Additionally, chlorhexidine must be protected from light which is not required in the case of the polymeric biguanide, and application of the latter to the appropriate support media leads to no discolouration.

When chlorhexidine and the polymeric biguanide are applied to cellulosic substrates, they exhibit similar activity to bacteria such as Pr. vulgaris, although the polymeric biguanide surprisingly shows greater activity against the clinically important *Ps. aeruginosa.*

Quaternary ammonium compounds have also been proposed for use in disposable non-woven materials to suppress odours and control micro-organisms. Generally, they suffer from pronounced foaming deficiencies and lack of substantivity leading to problems during application. They are also not particularly effective in controlling micro organisms in this particular application. This is especially true in the case of the reactive silicon based quaternary ammonium compound, commercially available as DC 5700 from Dow-Corning which has recently been recommended for such outlets (cf. American Dyestuffs Reporter, June 1984, p.35–45).

Various techniques have been proposed in the past for assessing body odours, and most have resorted to nasal assessment using panels of experts, e.g. odour control in mens socks using DC 5700 ref "A new durable Antimicrobial Finish for Textiles", R. L. Getting and B. L. Triplett, paper presented at the AATCC National Conference 1978, and more recently the use of polymeric biguanides in deodorant formulations claimed in U.S. Pat. No. 4,478,821 assigned to Gillette. These methods are not particularly sophisticated. In the American Dyestuff Reporter, June 1984, p.35–45, odour assessment based on the ureolytic activity of *Proteus mirabilis* and measurement of ammonia in the free-air space is described. This approach whilst being an improvement on the "nasal panel" methodology, lacks refinement and sensitivity, being dependent on pH and the buffering capacity of urine. Consequently, we have developed this approach further to enable the total ammonia content to be accurately measured, even from the earliest stage of bacterial ureolytic activity when all the ammonia generated is bound as inorganic and/or organic salts, and does not manifest itself in the free space above such liquids. This method is based on first determining the ureolytic activity of those micro organisms implicated in odour generation using the technique outlined below.

0.5 ml nutrient broth into which individual micro organisms had been repeatedly subcultured (containing approximately $10^8$ cfu/ml) was added to 9.5 ml synthetic urine devoid of ammonium ion. 1 ml of this inoculated urine was entered into a sterile closed vial and incubated at 36° C. The ammonia generated was determined after 6 hours and 24 hours by dilution with 9 ml 0.02N hydrochloric acid followed by millipore filtration, and the ammonium ion content determined by column chromatography using a Dionex chromatographic analyser. The ammonia content found in the samples is listed below (in ppm).

|  |  | 6 hrs | 24 hrs |
|---|---|---|---|
| *Entero bacteria* | *Klebsiella pneumoniae* | 36 | 420 |
|  | *Escherichia coli* | 28 | 100 |
|  | *Proteus vulgaris* | 500 | 1290 |
| Gram positive cocci | *Staphylococcus aureus* | 6 | 280 |
|  | *Streptococcus faecalis* | 3 | 74 |
| Anaerobes | *Lacto bacillus* sp. | 3 | 50 |
| Pseudomonads | *Pseudomonas aeruginosa* 1 | 1200 | 2220 |
|  | *Pseudomonas aeruginosa* 2 | 78 | 460 |
|  | *Pseudomonas aeruginosa* 3 | 34 | 380 |
|  | *Pseudomonas aeruginosa* 4 | 28 | 290 |
| Yeast | *Endomycopsis* (formerly *Candida*) *albicans* | 0 | 24 |

The invention is further illustrated by the following Examples in which all parts and percentages are by weight unless otherwise indicated.

EXAMPLE 1

The absorbent wadding material was stripped from an adult incontinence pad and 2.5 parts dispersed in 200 parts water by rapid agitation. Sufficient quantities of a 20% aqueous solution of a mixture of polyhexamethylene biguanide dihydrochlorides (PHMB), having number average molecular weights from 1300–2200, were added, at neutral pH, to separate samples of the absorbent wadding, to give 100, 500, 1000 and 3000 ppm of PHMB on the substrate. The PHMB was completely adsorbed. A control sample contained no PHMB but was otherwise treated as the test samples. Each sample was then cast into a paper sheet measuring approximately 7"×5", and dried on a steam heated calender drum.

Two 1" squares of each sheet were placed in a sterile petri dish and wetted with 1 part synthetic urine (pH 6.6). The wetted sheet was then inoculated with the gram-negative, ureolytic bacterium, *Proteus vulgaris* (ca $10^6$ cFu), and incubated at 37° C. Generation of ammonia was followed by monitoring the changes in pH. After 24 and 48 hours, the sheet derived from the sample impregnated with 1000 ppm PHMB showed no change of pH whereas the sheet derived from the control exhibited a marked increase in pH associated with the characteristic smell of ammonia.

EXAMPLE 2

When the *Proteus vulgaris* used in Example 1 was replaced by a wild bacterium isolated and cultured from a soiled infant's nappy, substantially similar results were obtained.

EXAMPLE 3

Absorbent paper exhibiting similar grammage (ca 100 gm/m$^2$) to the sheets cast from wadding material described in Example 1 was passed through aqueous solutions of PHMB at various concentrations, squeezed and dried on a hot calender drum to give the following concentrations of PHMB on the absorbent papers (cf. table below).

0.5 g. of the above papers were entered into a sterile closed vial and impregnated with 1 ml inoculated synthetic urine prepared by adding 0.5 ml broth culture of *Proteus vulgaris* to 9.5 ml urine. After incubation at 36° C., samples were removed at various times, and the ammonia generated determined by extraction into 9 ml 0.02N hydrochloric acid, and millipore filtered. The ammonia content was determined by chromatographic analysis and gave the following results expressed in ppm ammonia.

| Concn. PHMB applied (ppm) | Incubation (hours) | | | | | |
|---|---|---|---|---|---|---|
|  | 1 | 2 | 4 | 6 | 8 | 24 |
| 0 | 53 | 86 | 307 | 442 | 594 | 1564 |
| 125 | 32 | 61 | 224 | 446 | 400 | 640 |
| 250 | 30 | 42 | 64 | 147 | 210 | 133 |
| 500 | 20 | 25 | 36 | 40 | 30 | 119 |
| 1000 | 20 | — | — | — | 20 | 53 |
| 2000 | 20 | — | — | — | 20 | 40 |
| 3000 | 20 | — | — | — | 20 | 89 |

EXAMPLE 4

Absorbent papers containing 1000 ppm PHMB prepared as above were challenged with various micro organisms including a cocktail prepared by mixing equal parts of all eleven organisms. Incubation and analysis was carried out as described in Example 3 and gave the following results.

| Concn. PHMB applied (ppm) | Incubation (hours) | | | | | | | Challenging organism |
|---|---|---|---|---|---|---|---|---|
| | 2 | 4 | 6 | 8 | 13 | 18 | 24 | |
| 0 | 211 | 605 | 1190 | 1410 | 1860 | 2000 | 1870 | Ps. aeruginosa 1 |
| 1000 | 27 | 32 | 47 | 44 | 120 | 56 | 76 | Ps. aeruginosa 1 |
| " | | | 15 | | | | 23 | E. coli |
| " | | | 17 | | | | 18 | S. faecalis |
| " | | | 18 | | | | 14 | Lacto. bacillus |
| " | | | 18 | | | | 35 | P. vulgaris |
| " | | | 21 | | | | 24 | St. areus |
| " | | | 14 | | | | 16 | K. pneumoniae |
| " | | | 8 | | | | 10 | E. albicans |
| " | | | 26 | | | | 36 | Ps. aeruginosa 2 |
| " | | | 26 | | | | 34 | Ps. aeruginosa 3 |
| " | | | 18 | | | | 33 | Ps. aeruginosa 4 |
| 0 | 43 | 410 | 590 | 740 | 1110 | 1200 | 1400 | Cocktail |
| 1000 | 17 | 39 | 22 | 27 | 29 | 24 | 27 | Cocktail |

EXAMPLE 5

Example 4 was repeated except that the 0.5 g substrate was impregnated with 1.66 ml inoculated urine in place of the 1 ml used in Example 3, giving the following results.

| Concn. PHMB applied (ppm) | Incubation (hours) | | | | | | | Challenging organism |
|---|---|---|---|---|---|---|---|---|
| | 2 | 4 | 6 | 8 | 13 | 18 | 24 | |
| 0 | 280 | 840 | 1200 | 2040 | 2500 | 2770 | 2700 | Ps. aeruginosa 1 |
| 1000 | 65 | 110 | 230 | 110 | 83 | 119 | 156 | Ps. aeruginosa 1 |
| 0 | 37 | 151 | 366 | 874 | 1300 | 1390 | 1480 | Cocktail |
| 1000 | 16 | 17 | 19 | 17 | 21 | 45 | 35 | Cocktail |
| 1000 | 23 | 24 | 23 | 18 | 19 | 17 | 22 | St. aureus |
| 1000 | 12 | 10 | 13 | 10 | 15 | 19 | 21 | K. pneumoniae |

EXAMPLE 6

10 g wadding was stripped from a commercially available disposable nappy and dispersed in 800 ml water by rapid agitation. An aqueous solution of PHMB was added to give 1000 ppm and 1500 ppm PHMB on weight of substrate. The PHMB was rapidly and completely absorbed. Water was removed from the treated wadding by filtration and rotary evaporation, and the wadding "fluffed" by high speed air agitation. The wadding so obtained exhibited no discolouration, with excellent absorbency.

0.5 g samples of the treated wadding was entered into a closed sterile vial and impregnated with 1 ml inoculated synthetic urine, and analysed as in the foregoing examples to give the following results. Ammonia content expressed in ppm.

| Concn. PHMB applied (ppm) | Incubation (hours) | | | | | | | Challenging organism |
|---|---|---|---|---|---|---|---|---|
| | 2 | 4 | 6 | 8 | 13 | 18 | 24 | |
| 0 | 208 | 662 | 1272 | 1432 | 1542 | 1602 | 1522 | Pr. vulgaris |
| 1000 | 8 | 48 | 143 | 311 | 348 | 298 | 346 | Pr. vulgaris |
| 1500 | 0 | 0 | 0 | 10 | 22 | 86 | 135 | Pr. vulgaris |
| 0 | 22 | 270 | 732 | 1042 | 1122 | 1072 | 1212 | Cocktail of 11 micro organisms |
| 1000 | 0 | 0 | 152 | 330 | 418 | 446 | 378 | |
| 1500 | 0 | 0 | 0 | 27 | 21 | 72 | 52 | |

In the above example, as in the foregoing examples, the untreated substrate when contacted with urine containing a micro organism rapidly acquired an objectional urinal odour which becomes increasingly noticeable after 8 hours incubation. This is especially true when challenged with the cocktail of micro organisms.

The treated substrate containing PHMB remains completely free from such odours even after 24 hours and exhibits the freshness of damp domestic washing.

EXAMPLE 7

The absorbent paper containing 1000 ppm PHMB, following challenge with Pr. vulgaris and synthetic urine and incubated for 24 hours was pressed onto a nutrient agar plate, and the plate incubated overnight at 37° C. The plate displayed no microbial growth. A similar paper containing no PHMB when treated in the same manner resulted in heavy growth of the micro organism.

EXAMPLE 8

Absorbent papers (grammage 102 gm/m$^2$) were impregnated with PHMB and chlorhexidine by padding through the appropriate aqueous concentration of the bio-active compound, squeezing between mangles to give 120% liquor retention and dried on a heated calender drum. The aqueous solutions of biocide were calculated to give 1000 ppm of PHMB and chlorhexidine on the support.

0.5 g support were folded and placed in a sealed sterile vial, and challenged with 1 ml synthetic urine made by adding 0.5 ml overnight broth culture of Ps. aeruginosa to 9.5 ml synthetic urine. After incubation at 36° C., the ammonia generated was extracted into 9 ml 0.02N hydrochloric acid, millipore filtered and analysed. The results are tabulated below in ppm ammonia.

| Biocide added (ppm) | Incubation (hours) | | | | | | |
|---|---|---|---|---|---|---|---|
| | 2 | 4 | 6 | 8 | 13 | 18 | 24 |
| 0 | 21 | 20 | 62 | 104 | 200 | 305 | 386 |
| 1000 ppm PHMB | 21 | 17 | 19 | 29 | 24 | 29 | 27 |
| 1000 ppm chlorhexidine | NA | NA | NA | NA | 19 | 26 | 280 |
| 1000 ppm Arquad 18 | 15 | 20 | 60 | 118 | 221 | 352 | 433 |

-continued

| Biocide added | Incubation (hours) | | | | | | |
|---|---|---|---|---|---|---|---|
| (ppm) | 2 | 4 | 6 | 8 | 13 | 18 | 24 |
| 3000 ppm DC 5700 | 15 | 18 | 51 | 113 | 240 | 373 | 418 |

NA — not available.
Arquad 18 is the octadecyl trimethyl ammonium chloride supplied by Armour Chemical Division.
DC 5700 is trimethoxy silyl propyl octadecyl dimethyl ammonium chloride, sold by Dow Corning.

EXAMPLE 9

Papers were prepared by taking wadding material stripped from a commercially available disposable nappy (2.5 g) and dispersing in 200 ml water by rapid agitation. 5.0 ml of 0.05% aqueous solution of PHMB and chlorhexidine were added respectively, stirred for a further 5 minutes, and the treated pulp cast into a hand sheet by discharging onto a wire screen, pressing to express surplus water and drying on a hot calender drum. 0.5 g of the paper (90 g/m$^2$) so obtained were treated as in Example 8 to give the following results.

| Biocide added | Incubation (hours) | | | |
|---|---|---|---|---|
| (ppm) | 2 | 4 | 8 | 24 |
| 1000 ppm PHMB | 45 | 38 | 38 | 102 |
| 1000 ppm chlorhexidine | 33 | 30 | 87 | 327 |

EXAMPLE 10

Absorbent paper (ca. 100 g/m$^2$) was impregnated by padding and squeezing to give the following uptake of bio-active compound as listed below. 0.5 g of the treated papers were challenged with 1 ml synthetic urine containing *Pr. vulgaris* in place of the *Ps. aeruginosa* used in Example 8, otherwise the conditions and analysis were similar to those described in Example 8. The ammonia generated is as listed in the table.

| Biocide added | Incubation (hours) | | | | | | |
|---|---|---|---|---|---|---|---|
| (ppm) | 2 | 4 | 6 | 8 | 13 | 18 | 24 |
| 0 | 49 | 82 | 170 | 184 | 520 | 580 | 700 |
| 1000 ppm PHMB | 27 | 28 | 33 | 33 | 60 | 62 | 75 |
| 2000 ppm chlorhexidine | 19 | 24 | 26 | 23 | 38 | 63 | 52 |
| 1000 ppm Arquad 18 | 18 | 26 | 29 | 31 | 68 | 66 | 88 |
| 3000 ppm DC 5700 | 34 | 47 | 60 | 77 | 150 | 210 | 200 |

EXAMPLE 11

A disposable nappy was sprayed with an aqueous solution of PHMB such as to produce a loading of 1000 ppm PHMB relative to the weight of wadding. After drying, a 0.5 g sample comprising "fluffed" wadding and cover stock material was evaluated in a similar manner to that described in Example 4. When challenged with *Ps. aeruginosa* and a cocktail of 11 organisms, it exhibited similar results. As in previous examples, the material treated with PHMB when challenged with either the single organism or the cocktail produced no objectionable odours even after 24 hours incubation, whereas the untreated substrate when so treated yield the expected objectionable urinal odours even after 8 hours incubation.

EXAMPLE 12

A commercially available incontinence pad whose construction comprised a plastic backing, coverstock and creped paper as absorbent medium was impregnated with PHMB by padding through an aqueous solution of the biocide followed by squeezing and drying on a hot calender. The biocide retained was 1000 ppm PHMB.

0.5 g of this material was treated as described in Example 4, and gave similar results.

I claim:

1. A non-woven material treated with a linear polymeric biguanide in which the recurring unit is of the formula:

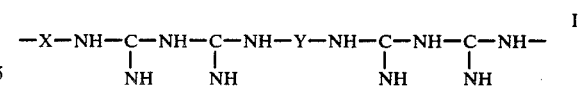

wherein X and Y, which may be the same or different, represent bridging groups in which the total number of carbon atoms in X and Y taken together, directly interposed between the pairs of nitrogen atoms linked thereby, is from 10 to 16, or the salt thereof with an acid.

2. A non-woven material according to claim 1 wherein the groups X and Y are polymethylene groups containing from 3 to 12 carbon atoms.

3. A non-woven material according to claim 1 wherein X and Y are hexamethylene groups.

4. A non-woven material according to claim 1 wherein the polymeric biguanide has a molecular weight in the range 500 to 20,000.

5. A non-woven material according to claim 1 wherein the polymeric biguanide contains from 5 to 12 biguanide units.

6. A non-woven material according to claim 1 wherein the polymeric biguanide is present at a concentration ranging from 500 to 5000 ppm.

7. A non-woven material according to claim 1 wherein the polymeric biguanide is a mixture of polyhexamethyle biguanide dihydrochlorides having number average molecular weights from 1300–2200.

8. A non-woven material according to claim 1 in the form of an article for the collection of human body emissions.

9. A non-woven material according to claim 8 wherein the article is a disposable nappy, a disposable feminine hygiene pad, a paper handkerchief or an incontinence pad.

* * * * *